US012599357B2

(12) United States Patent
Fan et al.

(10) Patent No.: US 12,599,357 B2
(45) Date of Patent: Apr. 14, 2026

(54) ULTRASOUND AUTOMATED DETECTION AND DISPLAY METHOD OF CRANIAL ABNORMAL REGIONS

(71) Applicant: Shantou Institute of Ultrasonic Instruments Co., Ltd., Shantou (CN)

(72) Inventors: Liexiang Fan, Shantou (CN); Delai Li, Shantou (CN); Zehang Cai, Shantou (CN); Bin Li, Shantou (CN); Zhonghong Wu, Shantou (CN); Yu Wang, Shantou (CN); Jinhao Lin, Shantou (CN); Shaohui Chen, Shantou (CN); Weiwu Chen, Shantou (CN); Jingfeng Guo, Shantou (CN); Yijie Chen, Shantou (CN)

(73) Assignee: Shantou Institute of Ultrasonic Instruments Co., Ltd., Shantou (CN)

( * ) Notice: Subject to any disclaimer, the term of this patent is extended or adjusted under 35 U.S.C. 154(b) by 279 days.

(21) Appl. No.: 18/610,676

(22) Filed: Mar. 20, 2024

(65) Prior Publication Data

US 2024/0225587 A1 Jul. 11, 2024

Related U.S. Application Data

(63) Continuation of application No. PCT/CN2022/073430, filed on Jan. 24, 2022.

(30) Foreign Application Priority Data

Jan. 14, 2022 (CN) .......................... 202210042593.2

(51) Int. Cl.
*A61B 8/08* (2006.01)
*A61B 8/00* (2006.01)
*G06T 7/00* (2017.01)

(52) U.S. Cl.
CPC ............ *A61B 8/0808* (2013.01); *A61B 8/466* (2013.01); *A61B 8/5223* (2013.01); *A61B 8/523* (2013.01);
(Continued)

(58) Field of Classification Search
None
See application file for complete search history.

(56) References Cited

U.S. PATENT DOCUMENTS 10,213,183 B2 * 2/2019 Zou ...................... A61B 8/0866
10,702,240 B2 * 7/2020 Zou ........................ A61B 8/483
(Continued)

OTHER PUBLICATIONS

Chen et al., Registration-Based Segmentation of Three-Dimensional Ultrasound Images for Quantitative Measurement of Fetal Craniofacial Structure, Ultrasound in Medicine & Biology, vol. 38, Issue 5, 2012, pp. 811-823, ISSN 0301-5629. (Year: 2012).*
(Continued)

*Primary Examiner* — Sath V Perungavoor
(74) *Attorney, Agent, or Firm* — Westbridge IP LLC

(57) ABSTRACT

An ultrasound automated detection and display method of cranial abnormal regions includes: firstly, a skull surface model is constructed; then contour detection is carried out based on a two-dimensional ultrasonic image to obtain a skull contour curve; fitting is carried out on the contour curve and the skull surface model to determine whether the two-dimensional ultrasonic image has symmetry characteristics or not; finally, similarity comparison calculation is carried out on two mutually symmetrical regions by utilizing the symmetry characteristics of the two-dimensional image, so that whether an abnormal region exists and the location of the abnormal region is determined. The method has the advantages that a skull surface model is constructed before detecting a cranial contour curve on a two-dimensional ultrasonic image.

4 Claims, 2 Drawing Sheets

(52) U.S. Cl.
     CPC .. *G06T 7/0012* (2013.01); *G06T 2207/10132*
          (2013.01); *G06T 2207/30008* (2013.01)

(56)                   References Cited

U.S. PATENT DOCUMENTS

| | | | | |
|---|---|---|---|---|
| 11,229,419 B2* | 1/2022 | Zou | ....................... | G06F 18/214 |
| 11,534,134 B2* | 12/2022 | Zou | ....................... | A61B 8/0866 |
| 12,329,567 B2* | 6/2025 | Fan | ....................... | A61B 8/0808 |
| 2007/0287915 A1* | 12/2007 | Akaki | ....................... | A61B 8/00 |
| | | | | 600/443 |
| 2011/0028843 A1* | 2/2011 | Hyun | ....................... | G06T 7/38 |
| | | | | 600/443 |
| 2011/0125016 A1* | 5/2011 | Lazebnik | ............... | A61B 8/463 |
| | | | | 600/443 |
| 2011/0158490 A1* | 6/2011 | Cong | ..................... | A61B 8/543 |
| | | | | 382/128 |
| 2011/0224546 A1* | 9/2011 | Lee | ....................... | A61B 8/0866 |
| | | | | 600/443 |
| 2015/0375013 A1* | 12/2015 | Lachaine | ................. | A61B 8/58 |
| | | | | 600/439 |
| 2021/0256698 A1* | 8/2021 | Chang | ................... | G06T 7/0014 |
| 2023/0225700 A1* | 7/2023 | Fan | ....................... | A61B 8/4477 |
| | | | | 600/437 |
| 2024/0225587 A1* | 7/2024 | Fan | ....................... | G06T 7/0012 |

OTHER PUBLICATIONS

Deng et al., A novel skull registration based on global and local deformations for craniofacial reconstruction, Forensic Science International, vol. 208, Issues 1-3, 2011, pp. 95-102, ISSN 0379-0738. (Year: 2011).*

Liao et al., Three-dimensional reconstruction of cranial defect using active contour model and image registration. Med Biol Eng Comput 49, 203-211, 2011. (Year: 2011).*

* cited by examiner

Partial contour formed by intersection
between image plane and skull

Ultrasound probe
scanning window

Image plane

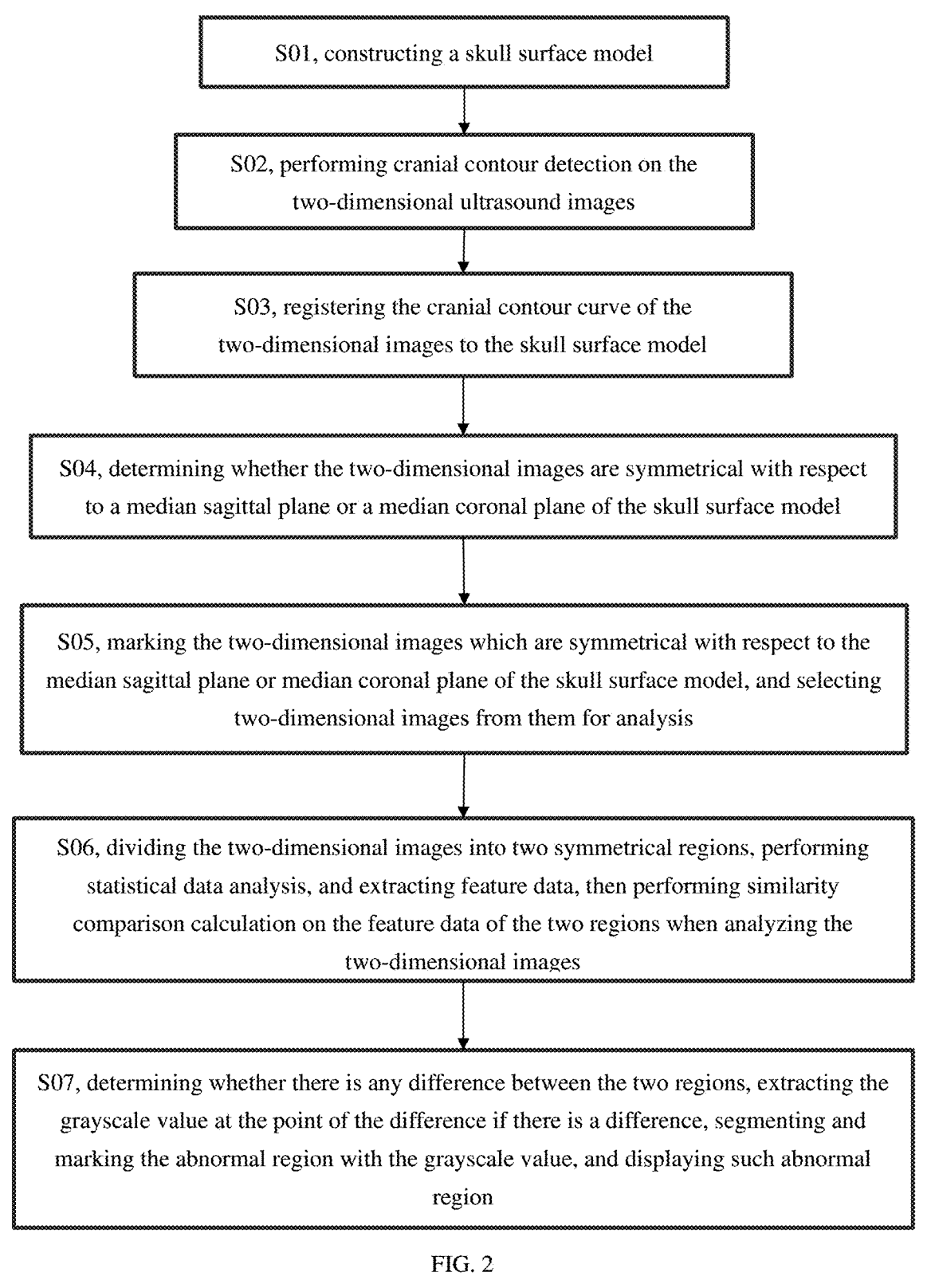

S01, constructing a skull surface model

↓

S02, performing cranial contour detection on the two-dimensional ultrasound images

↓

S03, registering the cranial contour curve of the two-dimensional images to the skull surface model

↓

S04, determining whether the two-dimensional images are symmetrical with respect to a median sagittal plane or a median coronal plane of the skull surface model

↓

S05, marking the two-dimensional images which are symmetrical with respect to the median sagittal plane or median coronal plane of the skull surface model, and selecting two-dimensional images from them for analysis

↓

S06, dividing the two-dimensional images into two symmetrical regions, performing statistical data analysis, and extracting feature data, then performing similarity comparison calculation on the feature data of the two regions when analyzing the two-dimensional images

↓

S07, determining whether there is any difference between the two regions, extracting the grayscale value at the point of the difference if there is a difference, segmenting and marking the abnormal region with the grayscale value, and displaying such abnormal region

FIG. 2

ULTRASOUND AUTOMATED DETECTION AND DISPLAY METHOD OF CRANIAL ABNORMAL REGIONS

CROSS-REFERENCE TO RELATED APPLICATIONS

The present application is a continuation application of International Application No. PCT/CN2022/073430, filed on Jan. 24, 2022, which claims priority to Chinese Patent Application No. 202210042593.2, filed on Jan. 14, 2022. All of the aforementioned applications are incorporated herein by reference in their entireties.

TECHNICAL FIELD

The application relates to the field of ultrasonic detection, in particular to an ultrasound automated detection and display method of cranial abnormal regions.

BACKGROUND

Cranial ultrasound scan is a routine clinical practice, particularly with wide application in neonatal clinical monitoring. Cranial ultrasound scan is mainly used for diagnosis of symptoms such as intraventricular hemorrhage (IVH), pericerebral hemorrhage infarction periventricular hemorrhagic infarction (PVHI), post-hemorrhagic ventricular dilatation (PVHD), and cystic periventricular leukomalacia (cPVL). In traditional diagnosis methods, sonographers rely on knowledge and experience to identify abnormalities in images; with the continuous development of computer technology, the use of computers to automatically analyze and diagnose images may reduce the burden and improve the efficiency of doctors' diagnosis.

However, the conventional processing and popular machine learning methods cannot be effectively used for the analysis and diagnosis of cranial ultrasound images due to the complexity of cranial ultrasound images, which is represented by the uncertainty of abnormal grayscale values of brain images. That is, higher grayscale value for new bleeding points, whose range is close to or higher than the grayscale of normal tissues; and lower grayscale value for old bleeding points, whose range is lower than the grayscale of normal tissues.

SUMMARY

The application aims at providing an ultrasound automated detection and display method of cranial abnormal regions, specifically, providing an ultrasound automated detection and display method of cranial abnormal regions that improves the accuracy of diagnosis.

In order to achieve that above object, this application adopts the follow technical solution: the automated detection and display method of ultrasonic abnormal brain regions comprises the following steps:

S01, constructing a skull surface model using ultrasonic images obtained by performing ultrasonic scanning on a skull;

S02, performing cranial contour detection on the two-dimensional ultrasound images obtained by performing ultrasound scanning on the skull, and obtaining a cranial contour curve of the two-dimensional images;

S03, registering the cranial contour curve of the two-dimensional images obtained in step S02 to the skull surface model obtained in step S01 to determine the location of the two-dimensional images on the skull surface model;

S04, determining whether the two-dimensional images are symmetrical with respect to a median sagittal plane or a median coronal plane of the skull surface model according to the location of the two-dimensional images obtained in step S03 on the skull surface model;

S05, marking the two-dimensional images which are symmetrical with respect to the median sagittal plane or median coronal plane of the skull surface model in step S04, and selecting two-dimensional images from them for analysis according to analysis requirements;

S06, dividing the two-dimensional images into two symmetrical regions, performing histogram statistics or grayscale co-occurrence matrix calculation on images of the two regions to obtain statistical data, performing normalization processing on the statistical data of the two regions to extract feature data, and then performing similarity comparison calculation on the feature data of the two regions when analyzing the two-dimensional images; and S07, determining whether there is any difference between the two regions according to the calculated similarity, extracting the grayscale value at the point of the difference if there is a difference, segmenting and marking the abnormal region with the grayscale value as a guide and displaying such abnormal region.

Specifically, when contour detection is performed on the two-dimensional images in step S02, the contour between the skull and the cranial tissues is detected by using the grayscale or grayscale plus grayscale gradient value, and the contour is filtered and fitted to obtain the skull contour curve.

Specifically, when the skull surface model is constructed in step S01, three-dimensional ultrasound image scanning is performed on the brain; boundary detection on the three-dimensional ultrasound images between the skull and the cranial tissues is detected by using the grayscale or grayscale plus grayscale gradient value, and the boundary is filtered and fitted to obtain the skull surface model.

In another solution, when the skull surface model is constructed in step S01, two-dimensional ultrasound image scanning is performed on the brain; contour detection on the two-dimensional ultrasound images between the skull and the cranial tissues is detected by using the grayscale or grayscale plus grayscale gradient value, and the contours by using multiple two-dimensional ultrasonic images are filtered and fitted to obtain the skull surface model.

The application has the advantages that by constructing a skull surface model, a cranial contour curve is detected on two-dimensional ultrasonic images. The cranial contour curve and the skull surface model are used for fitting to determine the specific location of the two-dimensional images with an aim to selecting two-dimensional images with symmetrical characteristics, and the symmetry of the two-dimensional images is used for detecting, segmenting and displaying abnormal regions, therefore the accuracy of abnormal region detection is effectively improved.

BRIEF DESCRIPTION OF THE DRAWINGS

FIG. 2 is a general flow chart to implement the method described in this invention.

DETAILED DESCRIPTION OF THE EMBODIMENTS

Figure 1:
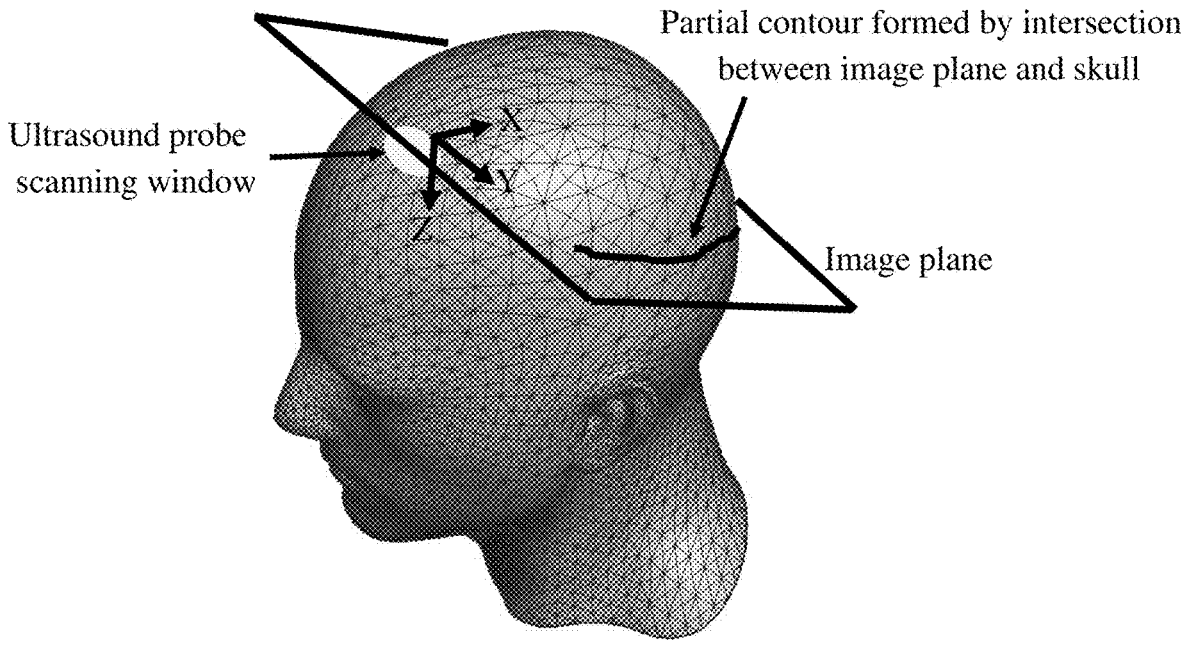
FIG. 1 is a schematic diagram of fitting a cranial contour curve and a skull surface model.

A general flow chart of realization of this invention is shown in FIG. 1, and two embodiments are described below.

Embodiment 1

An ultrasound automated detection and display method of cranial abnormal regions includes the following steps:
- S01, constructing a skull surface model using ultrasonic images obtained by performing ultrasonic scanning on a skull;
- S02, performing cranial contour detection on the two-dimensional ultrasound images obtained by performing ultrasound scanning on the skull, and obtaining a cranial contour curve of the two-dimensional images;
- S03, registering the cranial contour curve of the two-dimensional images obtained in step S02 to the skull surface model obtained in step S01 to determine the location of the two-dimensional images on the skull surface model;
- S04, determining whether the two-dimensional images are symmetrical with respect to a median sagittal plane or a median coronal plane of the skull surface model according to the location of the two-dimensional images obtained in step S03 on the skull surface model;
- S05, marking the two-dimensional images which are symmetrical with respect to the median sagittal plane or median coronal plane of the skull surface model in step S04, and selecting two-dimensional images from them for analysis according to analysis requirements;
- S06, dividing the two-dimensional images into two symmetrical regions, performing histogram statistics or grayscale co-occurrence matrix calculation on images of the two regions to obtain statistical data, performing normalization processing on the statistical data of the two regions to extract feature data, and then performing similarity comparison calculation on the feature data of the two regions when analyzing the two-dimensional images; and
- S07, determining whether there is any difference between the two regions according to the calculated similarity, extracting the grayscale value at the point of the difference if there is a difference, segmenting and marking the abnormal region with the grayscale value as a guide and displaying such abnormal region.

When contour detection is performed on the two-dimensional image in step S02, the contour between the skull and the cranial tissues is detected by using the grayscale or grayscale plus grayscale gradient value, and the contour is filtered and fitted to obtain the skull contour curve. Due to the strong emission of the skull in the ultrasound cranial image, the high grayscale value is presented in the image, and the edge of the image formed after detection can be easily detected, therefore the contour between the skull and the cranial tissues can be detected by using the grayscale or grayscale plus grayscale gradient value.

The skull surface model is constructed in step S01 as follows: three-dimensional ultrasound image scanning is performed on the brain; boundary detection on the three-dimensional ultrasound image between the skull and the cranial tissues is detected by using the grayscale or grayscale plus grayscale gradient value, and the boundary is filtered and fitted to obtain the skull surface model.

Embodiment 2

An ultrasound automated detection and display method of cranial abnormal regions includes the following steps:
- S01, constructing a skull surface model using ultrasonic images obtained by performing ultrasonic scanning on a skull;
- S02, performing cranial contour detection on the two-dimensional ultrasound images obtained by performing ultrasound scanning on the skull, and obtaining a cranial contour curve of the two-dimensional images;
- S03, registering the cranial contour curve of the two-dimensional images obtained in step S02 to the skull surface model obtained in step S01 to determine the location of the two-dimensional images on the skull surface model;
- S04, determining whether the two-dimensional images are symmetrical with respect to a median sagittal plane or a median coronal plane of the skull surface model according to the location of the two-dimensional images obtained in step S03 on the skull surface model;
- S05, marking the two-dimensional images which are symmetrical with respect to the median sagittal plane or median coronal plane of the skull surface model in step S04, and selecting two-dimensional images from them for analysis according to analysis requirements;
- S06, dividing the two-dimensional images into two symmetrical regions, performing histogram statistics or grayscale co-occurrence matrix calculation on images of the two regions to obtain statistical data, performing normalization processing on the statistical data of the two regions to extract feature data, and then performing similarity comparison calculation on the feature data of the two regions when analyzing the two-dimensional images; and
- S07, determining whether there is any difference between the two regions according to the calculated similarity, extracting the grayscale value at the point of the difference if there is a difference, segmenting and marking the abnormal region with the grayscale value as a guide and displaying such abnormal region.

When contour detection is performed on the two-dimensional image in step S02, the contour between the skull and the cranial tissues is detected by using the grayscale or grayscale plus grayscale gradient value, and the contour is filtered and fitted to obtain the skull contour curve. Due to the strong emission of the skull in the ultrasound cranial image, the high grayscale value is presented in the image, and the edge of the image formed after detection can be easily detected, therefore the contour between the skull and the cranial tissues can be detected by using the grayscale or grayscale plus grayscale gradient value.

When the skull surface model is constructed in step S01, two-dimensional ultrasound image scanning is performed on the brain; contour detection on the two-dimensional ultrasound image between the skull and the cranial tissues is detected by using the grayscale or grayscale plus grayscale gradient value, and the contours by using multiple two-dimensional ultrasonic images are filtered and fitted to obtain the skull surface model.

Certainly the embodiments above are preferred for the present application only, but not intended to restrict the scope of use of the present application. Therefore, any equivalent changes made on the principles of the present application should be included in the protection scope of the present application.

What is claimed is:

1. An ultrasound automated detection and display method of cranial abnormal regions, comprising following steps:

S01, constructing a skull surface model using ultrasonic images obtained by performing ultrasonic scanning on a skull;

S02, performing cranial contour detection on the two-dimensional ultrasound images obtained by performing ultrasound scanning on the skull, and obtaining a cranial contour curve of the two-dimensional images;

S03, registering the cranial contour curve of the two-dimensional images obtained in step S02 to the skull surface model obtained in step S01 to determine the location of the two-dimensional images on the skull surface model;

S04, determining whether the two-dimensional images are symmetrical with respect to a median sagittal plane or a median coronal plane of the skull surface model according to the location of the two-dimensional images obtained in step S03 on the skull surface model;

S05, marking the two-dimensional images which are symmetrical with respect to the median sagittal plane or median coronal plane of the skull surface model in step S04, and selecting two-dimensional images from them for analysis according to analysis requirements;

S06, dividing the two-dimensional images into two symmetrical regions, performing histogram statistics or grayscale co-occurrence matrix calculation on images of the two regions to obtain statistical data, performing normalization processing on the statistical data of the two regions to extract feature data, and then performing similarity comparison calculation on the feature data of the two regions when analyzing the two-dimensional images; and S07, determining whether there is any difference between the two regions according to the calculated similarity, extracting the grayscale value at the point of the difference if there is a difference, segmenting and marking the abnormal region with the grayscale value as a guide and displaying such abnormal region.

2. The ultrasound automated detection and display method of cranial abnormal regions according to claim 1, wherein when contour detection is performed on the two-dimensional image in step S02, the contour between the skull and the cranial tissues is detected by using the grayscale or grayscale plus grayscale gradient value, and the contour is filtered and fitted to obtain the skull contour curve.

3. The ultrasound automated detection and display method of cranial abnormal regions according to claim 1, wherein when the skull surface model is constructed in step S01, three-dimensional ultrasound image scanning is performed on the brain; boundary detection on the three-dimensional ultrasound images between the skull and the cranial tissues is detected by using the grayscale or grayscale plus grayscale gradient value, and the boundary is filtered and fitted to obtain the skull surface model.

4. The ultrasound automated detection and display method of cranial abnormal regions according to claim 1, wherein when the skull surface model is constructed in step S01, two-dimensional ultrasound image scanning is performed on the brain; contour detection on the two-dimensional ultrasound image between the skull and the cranial tissues is detected by using the grayscale or grayscale plus grayscale gradient value, and the contours by using multiple two-dimensional ultrasonic images are filtered and fitted to obtain the skull surface model.

* * * * *